United States Patent [19]

Ten Wolde

[11] Patent Number: 5,016,781
[45] Date of Patent: May 21, 1991

[54] DEVICE WITH REPLACEABLE CONTAINER FOR ATOMIZING LIQUID

[75] Inventor: Anne W. Ten Wolde, Bentveld, Netherlands

[73] Assignee: Williams Trading B.V., AA Heemstede, Netherlands

[21] Appl. No.: 224,775

[22] PCT Filed: Oct. 20, 1987

[86] PCT No.: PCT/NL87/00028
§ 371 Date: Aug. 11, 1988
§ 102(e) Date: Aug. 11, 1988

[87] PCT Pub. No.: WO88/03033
PCT Pub. Date: May 5, 1988

[30] Foreign Application Priority Data

Oct. 21, 1986 [NL] Netherlands ............... 8602639

[51] Int. Cl.⁵ .................................. B67D 5/64
[52] U.S. Cl. .............................. 222/162; 222/183; 222/325; 222/383; 239/274
[58] Field of Search .......... 222/162, 183, 185, 181, 222/325, 383; 239/274

[56] References Cited

U.S. PATENT DOCUMENTS

| | | | |
|---|---|---|---|
| 2,534,465 | 12/1950 | Marini | 239/274 |
| 2,558,469 | 6/1951 | Travis | 239/274 X |
| 2,728,608 | 12/1955 | Marini . | |
| 2,821,435 | 1/1958 | Wenner | 239/274 |
| 3,224,644 | 12/1965 | Davis . | |
| 4,164,306 | 8/1979 | Perrin | 222/325 X |
| 4,166,553 | 9/1979 | Fraterrigo | 222/181 |
| 4,394,938 | 7/1983 | Frassanito | 222/325 X |
| 4,579,261 | 4/1986 | Arabian et al. | 239/274 X |

FOREIGN PATENT DOCUMENTS

| | | | |
|---|---|---|---|
| 0127573 | 6/1986 | European Pat. Off. . | |
| 1151924 | 2/1958 | France | 239/274 |
| 1240970 | 8/1960 | France . | |
| 2283732 | 4/1976 | France | 239/274 |
| 2366878 | 5/1978 | France . | |
| 2448353 | 9/1980 | France . | |
| 2537550 | 6/1984 | France . | |
| 7010889 | 1/1971 | Netherlands . | |
| 154424 | 6/1971 | Netherlands . | |
| 382922 | 12/1964 | Switzerland . | |
| 411055 | 5/1934 | United Kingdom . | |
| 933555 | 8/1963 | United Kingdom . | |
| 946018 | 1/1964 | United Kingdom . | |
| 1099695 | 1/1968 | United Kingdom . | |

*Primary Examiner*—Kevin P. Shaver
*Attorney, Agent, or Firm*—Bachman & LaPointe

[57] ABSTRACT

Device for atomizing a liquid, such as for refreshing a toilet, which device is provided with a double-action pump. A replaceable container containing the liquid to be atomized is provided. The container contains a suction line, a nonreturn valve and a connecting nipple by means of which the container can be inserted in a connecting opening of the housing which is permanently mounted, for example on a door, and in which the pump and atomizer are situated.

2 Claims, 2 Drawing Sheets

DEVICE WITH REPLACEABLE CONTAINER FOR ATOMIZING LIQUID

BACKGROUND OF THE INVENTION

The invention relates to a device for emitting a finely divided stream of liquid into the atmosphere from a replaceable container, which device is provided with a carrier with means for attaching the carrier to a support, means for detachably receiving and supporting a container containing liquid and also a suction line, projecting into the liquid, whose discharge end projects outside the container and works in combination with a pump which is also received in the carrier and has an actuating element which can work in combination with an element capable of moving with respect to the fixed carrier.

Such a device is known for example from Swiss Patent 382,922. Said known device is intended for periodically emitting a perfume or disinfectant or similar agent, for example in toilets and similar rooms every time the door which provides access to said room is opened or closed. In said known device, the pump consists of a housing with a piston which has an actuating rod projecting outside the housing with which the piston can be displaced against spring pressure, the air present in the cylinder of the pump then being forced through an atomizing opening to the outside. The suction line projecting into the container has a discharge end which debouches near the atomizing opening. The atomization takes place because the stream of air flowing across the discharge end of the feed line produces a low pressure in the suction line, as a result of which a quantity of liquid from the container is atomized. This occurs every time when the actuating rod of the piston runs up against the frame of the door when the door is closed.

The operation of such an atomizer is insufficiently reliable. In addition, it is not clear how, in said known device, the replaceable container and suction line can be brought into combined operation with each other without risk of leakage when fitting a full container or removing a not completely empty container. An atomizer which is based on the Pitot principle will also start to work increasingly more unsatisfactorily as the filling of the container decreases because the distance between the liquid level in the suction line and the atomizer becomes increasingly larger.

The object of the invention is to provide a device which operates reliably regardless of the degree of filling of the container in which the container can easily be replaced without risk to the environment and which lacks the drawbacks of the known device.

SUMMARY OF THE INVENTION

According to the invention this object is achieved in that the discharge end of the suction line debouches into a fitting which is provided with a nonreturn valve preventing return flow and which forms part of the container and fits so as to form a seal into a recess in the pump housing, which recess has a connection to the interior of the pump situated on the compression side of the pump, piston or plunger, which pump housing has an atomizer with a nonreturn valve which is situated upstream of the atomizer and opens in the direction of the atomizer opening. The suction line, which in any case debouches with its discharge end into the fitting provided with a nonreturn valve, forms together with said fitting and nonreturn valve a component of the replaceable container. Installation of such a container is nothing more than inserting the fitting into the recess intended for the purpose in the pump housing. The removal takes place correspondingly in a simple manner.

Spillage during the installation or removal of a container cannot take place and may, in addition, be prevented in a simple manner by installing a closure cap over the fitting.

The pump which can be actuated during the opening and/or closing of, for example, a door, is a double-action pump of which only cylinder piston or the atomizer with nonreturn valve installed in the discharge are received in the carrier. After all, the valve in the suction line forms a part of the container. If a container is absent, the pump will not therefore work.

Attention is drawn to the fact that, from the Dutch Application 7010889, a device is known for atomizing a liquid in which the container is an aerosol container, i.e. a container with pressurized filling and a valve mechanism which forms part of the container. This device has the drawback which is inherent in aerosol containers since the pressurized gas fillings used therein are not harmless to the environment.

Attention is furthermore drawn to the fact that, from Dutch Patent Application 6504841, an atomizer is known which consists of a carrier which is provided with a screw thread to be installed on the neck of a bottle, to which carrier the suction line with nonreturn valve is attached and in which the pump is located, and also an atomizer with a nonreturn valve situated upstream thereof. This is not an atomizer which is permanently attached to a support but an atomizer with a press button to be operated manually. To install the atomizer on the bottle, the bottle has to be opened by removing the seal, after which the atomizer can be screwed onto it. These are operations which can be carried out at work top level. The device according to the type of the invention is situated, however, usually at the level of the lintel of a door frame, which makes replacement of the container containing liquid difficult. The invention provides a solution with which the replacement can take place easily and without risks.

Attention is also furthermore drawn to the fact that, from French Patent 1,240,970, a device is known which is intended for the same object as the device according to the invention, which device has a carrier with a cylinder and piston with actuating knob, onto which carrier a bottle can be screwed. The carrier has an atomizer which projects by means of a tube line into the interior of the bottle and is provided with a nonreturn valve. In this case, however, transfer of the liquid to be atomized takes place by increasing the pressure of the air situated above the liquid in the bottle by means of the piston. Such a device does not work efficiently and has an action which decreases as the liquid level in the bottle falls.

BRIEF DESCRIPTION OF THE DRAWINGS

The invention will now be explained in more detail by reference to the drawings.

DETAILED DESCRIPTION

Figure 1:
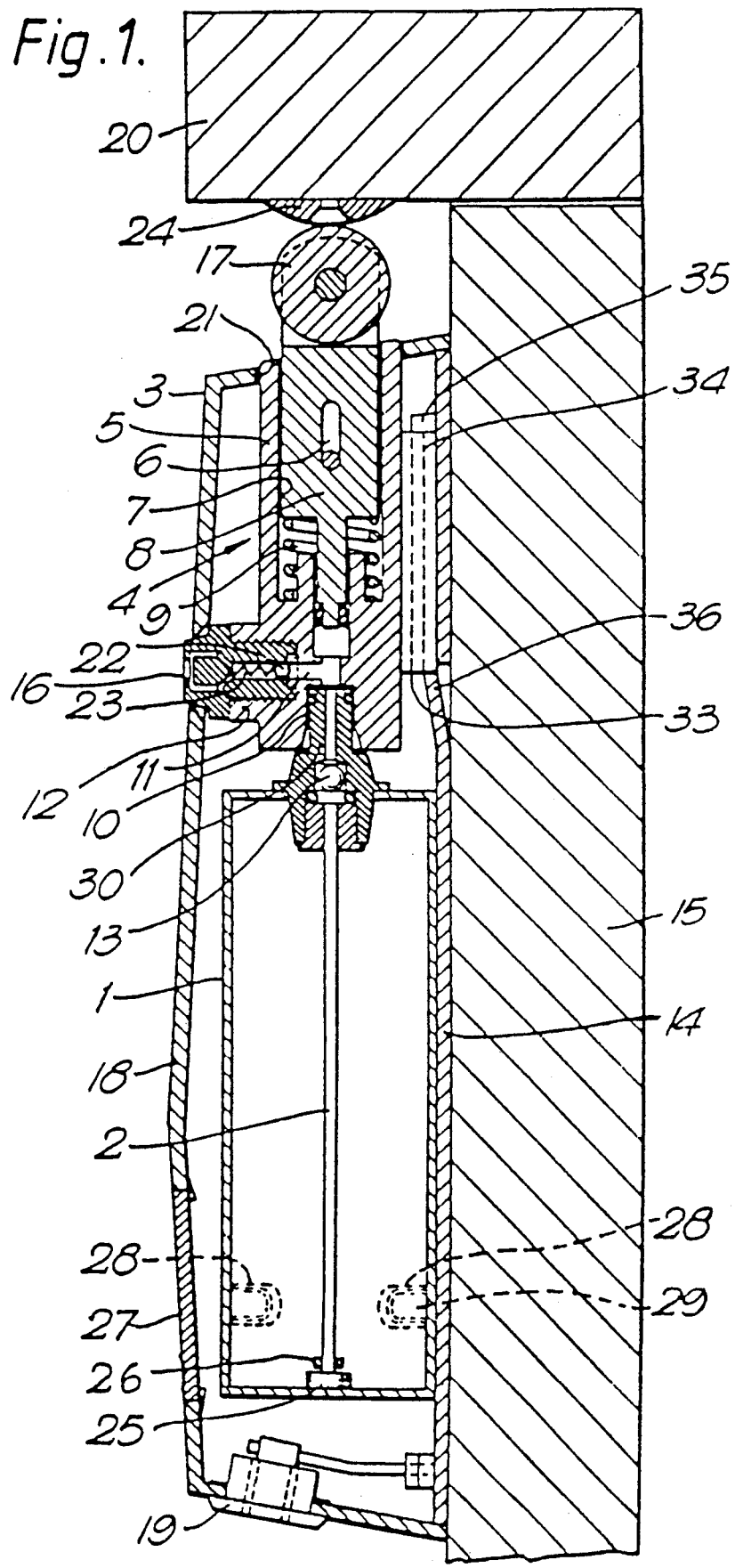
FIG. 1 shows an embodiment of the device according to the invention from the side in vertical section along the center line of the pump.
Figure 2:
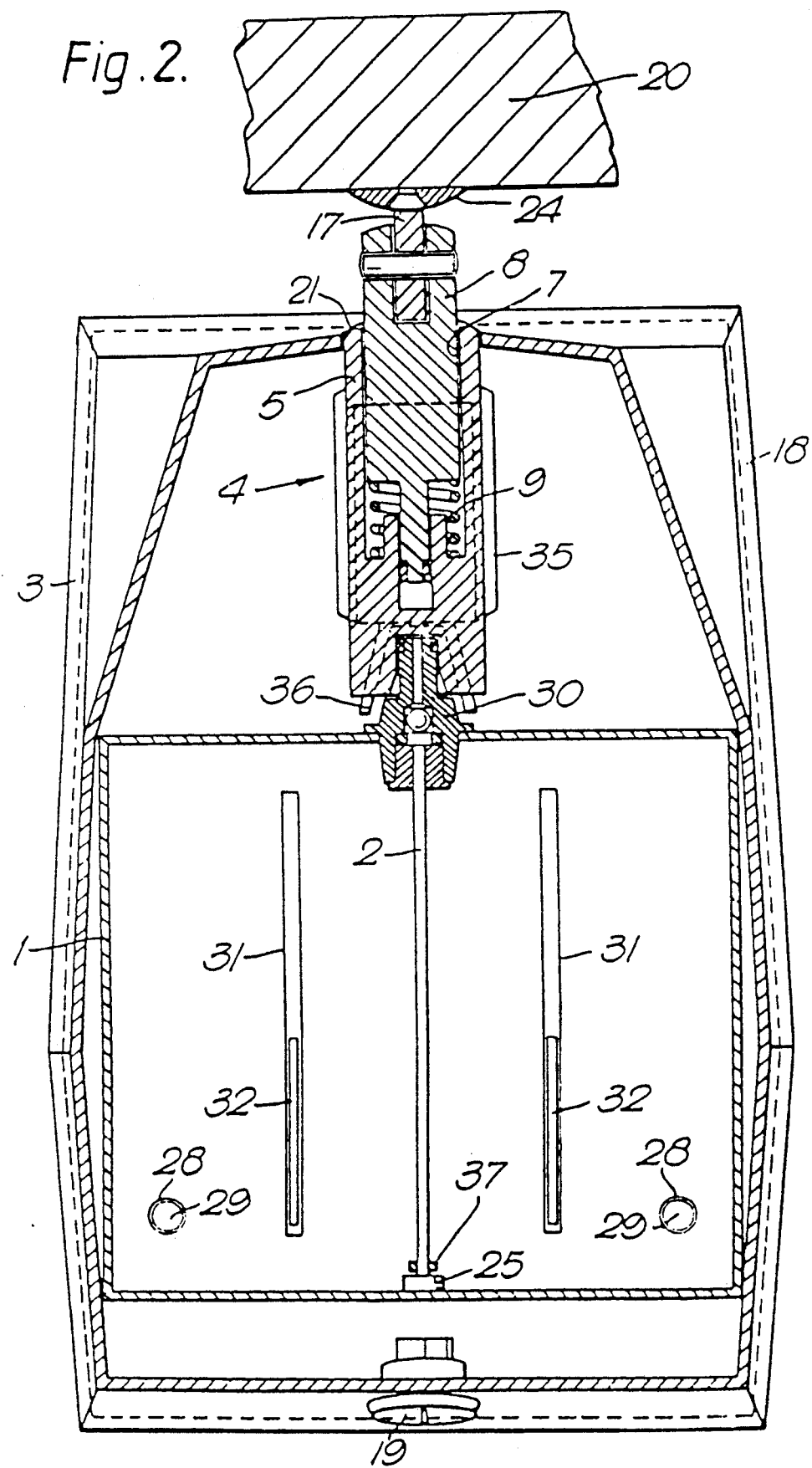
FIG. 2 shows a vertical section along the center line of the pump of the device shown in FIG. 1, which section is rotated through 90°.

FIGS. 1 and 2 show a toilet freshener for emitting a liquid spray from a replaceable container 1. Said container is provided with a suction tube 2. Said container 1 is placed in a carrier or housing 3 in which there is a pump which is indicated in its generality by 4. Said pump consists of a pump housing 5. Said pump housing has a vertical bore 7 in which there is a rod 8 which is displaceable in the bore 7 and acts in combination with a compression spring 9, which holds the rod 8 in its highest position. Said rod 8 projects through an opening 21 of the housing 3 of the device. The rod carries at its top a roller 17 which can act in combination with a cam 24 which is mounted on the lintel 20 of a frame of the door 15 on which the housing 3 is mounted. Said mounting takes place by means of a back plate 14 which is mounted on the door and which has a lip 36 at its top over which the housing 3 is slid by means of a sliding shoe 33 with side flanges 34 between vertical guides 35 which project from the back plate 14.

Said back plate carries two pins 29 which can project into shallow cylindrical cavities 28 of the container 1 in order to hold the latter in the correct position. Any other means is conceiveable for supporting the container 1 in the housing 3.

The housing 3 may furthermore be secured in position with relation to the back plate 14 by means of a lock 19.

Every container 1 has a nipple 30 in its top wall. This contains a nonreturn valve 13 which works in combination with a valve seating in the form of an O-ring and which permits outward flow via the suction line 2 which projects into the nipple but prevents return flow. Said nipple projects with a light drive fit into an opening, which becomes somewhat wider in the downward direction, of the pump housing 5.

The pump in the pump housing consists of a piston which forms one complete whole with the rod 8 but has an appreciably smaller diameter and projects at its bottom with a sealing ring into the part of the bore 7 having smaller diameter. Between the piston and the connecting opening for the nipple is the double-action chamber of the pump. This double-action chamber is formed by the suction channel 10 in the nipple and from the T-shaped section 11 which debouches into a horizontal bore 12 into which a nipple is screwed which is provided with a nonreturn valve 22 with pressure spring 23 and atomizer 16.

The suction tube 2 works in combination with a filter 25 at its bottom.

A float 26 by means of which the liquid level in a container consisting of transparent material can be inspected somewhat more exactly via the window 27 is displaceable along the suction tube.

The container may furthermore be provided in addition with grooves 31 in the front and/or back face of the container which can work in combination with ribs 32 of the back plate 14 to promote the precise positioning of the container.

The device described operates as follows:

When the door 15 is closed the small wheel 17 of the rod 8 runs up against the cam 24, as a result of which the piston is forced to execute a compression stroke and will thus atomize the liquid present in the chamber 11 via the nonreturn valve 22 and the atomizer 16.

When the door is opened, the spring 9 ensures that the piston executes a suction stroke, as a result of which liquid is introduced into the chamber 11 via the suction line 2 and the nonreturn valve 13. The liquid present in the latter is then atomized again when the door is closed.

I claim:

1. A device for emitting a finely divided stream of liquid into the atmosphere from a container, comprising:
    a support to be rigidly attached to a movable element;
    a housing releasably received on said support;
    a pump housing in said housing having a recess and bore therein;
    a container in said housing for liquid to be dispensed;
    a nipple with a first non-return valve and suction tube at the top of the container, with the suction tube extending into the container, said nipple fitting into the recess of the pump housing;
    a pump piston inside the pump housing bore, said piston having a piston part extending outside the pump housing;
    a fixed abutment cooperating with said piston part such that upon engagement of said piston part with said abutment the piston performs a pressure stroke against the pressure of a spring and during movement away from the abutment performs a return or suction stroke;
    wherein said pump housing communicates with the pump piston on one side and with the first non-return valve and suction tube on the other side;
    a pressure channel with a second non-return valve leading to an atomizer, said pressure channel communicating with the pump housing;
    wherein the container, nipple with suction tube and first non-return valve form a replaceable unit, the pump housing recess is adapted to slidably and sealingly receive the nipple and wherein the pump housing forms a unit with the housing; and
    wherein said support is a backing plate including pins and said container includes cavities, with said pins projecting into said cavities to hold the container in the correct position.

2. A device for emitting a finely divided stream of liquid into the atmosphere from a container, comprising:
    a support to be rigidly attached to a movable element;
    a housing releasably received on said support;
    a pump housing in said housing having a recess and bore therein;
    a container in said housing for liquid to be dispensed;
    a nipple with a first non-return valve and suction tube at the top of the container, with the suction tube extending into the container, said nipple fitting into the recess of the pump housing;
    a pump piston inside the pump housing bore, said piston having a piston part extending outside the pump housing;
    a fixed abutment cooperating with said piston part such that upon engagement of said piston part with said abutment the piston performs a pressure stroke against the pressure of a spring and during movement away from the abutment performs a return or suction stroke;
    wherein said pump housing communicates with the pump piston on one side and with the first non-return valve and suction tube on the other side;
    a pressure channel with a second non-return valve leading to an atomizer, said pressure channel communicating with the pump housing;

wherein the container, nipple with suction tube and first non-return valve form a replaceable unit, the pump housing recess is adapted to slidably and sealingly receive the nipple and wherein the pump housing forms a unit with the housing; and wherein said support is a backing plate wherein said container includes grooves and said backing plate includes ribs engaging with said grooves for positioning the container.

* * * * *